United States Patent [19]

Bernstein et al.

[11] Patent Number: 4,837,235

[45] Date of Patent: Jun. 6, 1989

[54] INDOLE AND INDAZOLE KETO SULPHONES AS LEUKOTRIENE ANTAGONISTS

[75] Inventors: Peter R. Bernstein, Wallingford, Pa.; Frederick J. Brown, Newark; Victor G. Matassa, Wilmington, both of Del.; Ying K. Yee, Kennett Square, Pa.

[73] Assignee: ICI Americas Inc., Wilmington, Del.

[21] Appl. No.: 919,781

[22] Filed: Oct. 16, 1986

[30] Foreign Application Priority Data

Oct. 17, 1985 [GB] United Kingdom ............... 8525657
Apr. 15, 1986 [GB] United Kingdom ............... 8609177

[51] Int. Cl.⁴ .................. A61K 31/535; C07D 231/56
[52] U.S. Cl. .............................. 514/234.5; 514/235.2; 514/253; 514/322; 514/323; 514/381; 514/406; 514/414; 514/419; 514/415; 544/140; 544/143; 544/144; 544/371; 544/373; 546/199; 546/201; 548/253; 548/371; 548/372; 548/405; 548/468; 548/494; 548/505; 548/506; 548/507; 548/510
[58] Field of Search ............... 548/371, 372, 253, 465, 548/468, 494, 505, 506, 507, 510; 514/406, 415, 234.5, 235.2, 253, 322, 323, 381, 414, 419; 544/140, 143, 144, 371, 373; 546/199, 201

[56] References Cited

U.S. PATENT DOCUMENTS 3,271,416  9/1966  Shen et al. .................... 548/494
3,415,841  12/1968  Nordmann et al. ............ 548/372
3,470,298  9/1969  Palazzo ......................... 514/407
4,499,299  2/1985  Bernstein et al. ............. 514/570

FOREIGN PATENT DOCUMENTS 234103  6/1964  Austria .
0166591  1/1986  European Pat. Off. .
0179619  4/1986  European Pat. Off. .
2854987  6/1980  Fed. Rep. of Germany .
403517  3/1966  France .
1049996  11/1966  United Kingdom .

OTHER PUBLICATIONS

Hannig, E., et al., *Pharmazie* 29, H. 10-11 (1974), pp. 685-686.
Krell, Robert D., *The Journal of Pharmacology and Experimental Therapeutics*, vol. 211, No. 2, pp. 436-443 (1979).
Marx, Jean L., *Science*, vol. 215, Mar. 12, 1982, pp. 1380-1382.
Denzlinger, C., et al., *Science*, vol. 230, pp. 330-332 (1985).
Cook, J. A., et al., *The Journal of Pharmacology and Experimental Therapeutics*, vol. 235, No. 2, pp. 470-474 (1985).
Derwent Abstract of Delgian Patent 671,445, Pub. Apr. 26, 1966.

*Primary Examiner*—Richard A. Schwartz
*Attorney, Agent, or Firm*—Rosemary M. Miano; Thomas E. Jackson

[57] ABSTRACT

This invention provides a series of novel keto sulfones of formula I

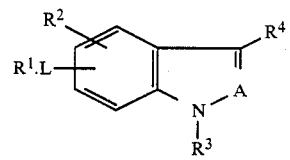

in which the group =A— is selected from =C(Ra)— and =N— and the other radicals have the meanings defined in the following specification.

The compounds of formula I are leukotriene antagonists. The invention also provides pharmaceutically acceptable salts of the formula I compounds; pharmaceutical compositions containing the formula I compound, or their salts, for use in the treatment of, for example, allergic or inflammatory diseases, or endotoxic or traumatic shock conditions; and processes for the manufacture of the formula I compounds, as well as intermediates for use in such manufacture.

17 Claims, No Drawings

INDOLE AND INDAZOLE KETO SULPHONES AS LEUKOTRIENE ANTAGONISTS

SUMMARY AND BACKGROUND OF THE INVENTION

This invention concerns novel heterocyclic compounds and, more particularly, novel indole and indazole keto sulphone derivatives, which antagonise the pharmacological actions of one or more of the arachidonic acid metabolites known as leukotrienes (hereafter referred to as "leukotriene antagonist properties"). The novel compounds are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions containing the novel compounds for use in such treatments and processes for the manufacture of the novel compounds.

In U.S. Pat. Nos. 3,271,416 and 3,470,298 there are described 5-acetamido-1-benzylalpha,2-dimethylindole-3-acetic acid derivatives and (5-acetamido-1-benzyl-1H-indazole-3-yl)oxyacetic acid derivatives, respectively, as antiinflammatory compounds. We have now discussed a series of indole and indazole derivatives which in the heterocyclic ring bear a benzyl group substituted by a keto sulphone moiety and in the benzenoid ring bear an amidic group and which unexpectedly possess the property of antagonizing one or more of the arachidonic acid metabolites known as leukotrienes, and this is the basis for our invention.

DESCRIPTION OF THE INVENTION

According to the invention there is provided a compound of formula I:

(Formula set out on pages following Examples) I wherein =A— is a group of formula =C(Ra)— or =N— in which Ra is hydrogen or (1–1C)alkyl;

the group $R^1.L$— is an amidic radical of formula $R^1.W.CO.NH$—, $R^1.W.CS.NH$— or $R^1.HN.CO$—, in which $R^1$ is (2–10C)alkyl optionally containing 1 or more fluorine substituents; or $R^1$ is phenyl-(1–6C)alkyl in which the (1–6C)alkyl moiety may optionally bear a fluoro or (1–4C)alkoxy substituent and in which the phenyl moiety may optionally bear a substituent selected from the group consisting of halogeno, (1–4C)alkyl, (1–4C)alkoxy and trifluoromethyl; or $R^1$ is (3–8C)cycloalkyl or (3–8C)cycloalkyl-(1–6C)alkyl, the cyclic moiety of any of which optionally may contain one unsaturated linkage and may optionally bear 1 or 2 (1–4C)alkyl substituents;

W is oxy, thio, imino or a direct link to $R^1$;

$R^2$ is hydrogen, halogeno, (1–4C)alkyl or (1–4C)alkoxy;

one of $R^3$ and $R^4$ is a radical of formula II:

(Formula set out on pages following Examples) II wherein

Rb is hydrogen, (1–4C)alkyl or (1–4C)alkoxy,

Rc is hydrogen, (1–4C)alkyl, (1–4C)alkoxy, trifluoromethyl or halogeno, and

M is hydrogen, cyano, (1–4C)alkoxycarbonyl, carbamoyl, N-phenylcarbamoyl (in which the phenyl may optionally bear a substituent), N-(1–4C)alkylcarbamoyl, N,N-di[(1–4C)alkyl]carbamoyl or (1–6C)alkanoyl;

and the other of $R^3$ and $R^4$ is hydrogen, halogeno (except for $R^3$), (3–8C)cycloalkyl, (3–8C)cycloalkyl-(1–4C)alkyl, or (1–10C)alkyl optionally containing one or two double or triple bonds, said (1–10C)alkyl additionally optionally bearing a substituent P selected from a group consisting of cyano, carboxy, 1H-tetrazol-5-yl, (1–4C)alkoxy, (1–4C)alkoxycarbonyl, carbamoyl of formula CONRdRe, ureido of formula NRfCONRdRe, carbamoyloxy of formula OCONRdRe, a carbamate of formula NRfCOORg, acylamino of formula NRfCORg, acyloxy of formula OCORg, and (optionally oxidized) thio group of formula $S(O)_nRg$ in which Rd is chosen from a group consisting of hydrogen, (1–6C)alkyl, and phenyl, the phenyl moiety of which may optionally bear 1 or 2 substituents selected from a group consisting of halogeno, (1–4C)alkyl, (1–4C)alkoxy and trifluoromethyl, and Re and Rf are independently chosen from a group consisting of hydrogen and (1–6C)alkyl, or Rd and Re together with the adjacent nitrogen form a pyrrole, pyrrolidine, piperidine, morpholine, piperazine or N-(1–6C)alkylpiperazine ring, Rg is chosen from a group consisting of (1–4C)alkyl and phenyl, the phenyl moiety of which may optionally bear 1 or 2 substituents selected from a group consisting of halogeno, (1–4C)alkyl, (1–4C)alkoxy and trifluoromethyl, and n is the integer 0, 1 or 2;

or a pharmaceutically acceptable salt thereof.

It will be appreciated that certain of the compounds of formula I, for example those wherein $R^1$ contains as asymmetrically substituted carbon atom, may exist in, and be isolated in, optically-active and racemic forms. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example by resolution of the racemic form or by synthesis from optically-active starting materials) and how to determine the leukotriene antagonist properties by the standard tests described hereinafter.

In this specification Ra, Rb, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example "alkylene" and "alkenylene" et cetera. Halogeno is fluoro, chloro, bromo or iodo.

Included in the ranges and values for the generic radicals are those wherein:

Ra is hydrogen or methyl;

the group $R^1.L$— is an amidic radical of formula $R^1.W.CO.NH$— or $R^1.NH.CO$—, in which $R^1$ is selected from a group consisting of (a) (3–7C)alkyl optionally containing 1 or more fluorine substituents; (b) phenyl-(1–4C)alkyl in which the (1–4C)alkyl moiety may optionally bear a fluoro or (1–4C)alkoxy substituent and in which the phenyl moiety may optionally bear a substituent selected from the group consisting of halogeno, (1–4C)alkyl, (1–4C)alkoxy and trifluoromethyl; and (c) (3–6C)cycloalkyl or (3–6C)cycloalkyl-(1–4C)alkyl, the cyclic moiety of any of which optionally may contain one unsaturated linkage and may optionally bear 1 or 2 (1–4C)alkyl substituents, and W is oxy, imino or a direct link to $R^1$;

$R^2$ is hydrogen, halogeno, methyl or methoxy;

Rb is meta to the carbonyl group and is hydrogen or (1–4C)alkoxy;

Rc is hydrogen, (1–4C)alkyl or halogeno;

M is hydrogen, cyano, (1–2C)alkoxycarbonyl, carbamoyl, N-(1–2C)alkylcarbamoyl, or (1–2C)alkanoyl;

and the other of $R^3$ and $R^4$ is hydrogen, halogeno (provided that $R^3$ may not be halogeno), (3–6C)cycloalkyl, (3–6C)cycloalkyl-(1–2C)alkyl, or (1–5C)alkyl optionally containing one double or triple bond, said (1–5C)alkyl additionally optionally bearing a substituent P selected from a group consisting of cyano, carboxy, 1H-tetrazol-5-yl, (1–2C)alkoxy, (1–2C)alkoxycarbonyl, carbamoyl of formula CONRdRe, and an oxidized thio group of formula $S(O)_n$Rg in which (1) Rd is chosen from a group consisting of hydrogen, (1–4C)alkyl, and phenyl, the phenyl moiety of which may optionally bear 1 or 2 substituents selected from a group consisting of halogeno, (1–4C)alkyl, (1–4C)alkoxy and trifluoromethyl; and Re is chosen from a group consisting of hydrogen and (1–4C)alkyl; or (2) Rd and Re together with the adjacent nitrogen form a piperidine, morpholine, piperazine or N-(1–2C)alkylpiperazine ring;

Rg is chosen from a group consisting of (1–4C)alkyl and phenyl, the phenyl moiety of which may optionally bear 1 or 2 substituents selected from a group consisting of halogen, (1–4C)alkyl, (1–4C)alkoxy and trifluoromethyl; and n is the integer 1 or 2;

as well as those wherein:

Rd and Re are independently chosen from a group consisting of hydrogen and (1–4C)alkyl; and Rg is (1–4C)alkyl.

Particular values for the generic radicals described as ranges above under Ra, Rb, $R^1$, $R^2$, M et cetera are as follows:

A particular value for Ra, Rb, Rc or $R^2$ when it is (1–4C)alkyl is, for example, methyl or ethyl.

A particular value for $R^2$, Rb or Rc when it is (1–4C)alkoxy is, for example, methoxy or ethoxy.

A particular value for $R^2$ or Rc when it is halogeno is, for example, fluoro, chloro or bromo.

A particular value for $R^3$ or $R^4$ when it is (1–10C)alkyl is, for example, methyl, ethyl, propyl, isopropyl, butyl, isobutyl, sec-butyl, 3-methylbutyl, pentyl or hexyl; when $R^3$ or $R^4$ is an alkyl containing 1 or 2 double or triple bonds, a particular value is, for example, vinyl, allyl, 1-propenyl, 2-methylallyl, 3-methylbut-2-enyl, 1,3-butadienyl, 1,3-pentadienyl, 2-propynyl or 3-butynyl, said alkyl group additionally optionally bearing a substituent P as defined above.

Particular values for an optional substituent P, or parts thereof, include for example:

for (1–4C)alkoxy: a member selected from the group consisting of methoxy and ethoxy;

for (1–4C)alkoxycarbonyl: a member selected from the group consisting of methoxycarbonyl, ethoxycarbonyl and isopropoxycarbonyl;

for Rd, Re, Rf, or the N-substituent of a piperazine when it is (1–6C)alkyl: a member selected from the group consisting of methyl, ethyl, propyl, isopropyl, butyl, t-butyl and pentyl;

for Rg when it is (1–4C)alkyl: a member selected from the group consisting of methyl, ethyl and propyl; and for optional substituents which may be present on a phenyl moiety of Rd or Rg: a member selected from the group consisting of those defined below in connection with a phenyl moiety in $R^1$.

A particular value for $R^3$ or $R^4$ when it is (3–8C)cycloalkyl is, for example, cyclopropyl, cyclopentyl or cyclohexyl; when it is (3–8C)cycloalkyl(1–4C)alkyl is, for example, cyclopropylmethyl, cyclopentylmethyl or cyclohexylmethyl; and when it is halogeno is, for example, chloro or bromo.

A particular value for $R^1$ when it is (2–10C)alkyl is, for example, ethyl, propyl, isopropyl, butyl, isobutyl, sec-butyl, t-butyl, pentyl, 1-ethylpropyl, hexyl, heptyl, 1-ethylpentyl or nonyl; and when it contains 1 or more fluorine substituents is, for example, 2,2,2-trifluoroethyl.

Particular values for $R^1$ when it is phenyl(1–6C)alkyl include, for example, benzyl, 1-phenylethyl, 2-phenylethyl, 1-phenylpropyl, 2-phenylpropyl, 3-phenylpropyl, 1-methyl-1-phenylethyl, 1-phenylbutyl and 1-phenylpentyl; and a particular value for an optional (1–4C)alkoxy substituent on the (1–6C)alkyl moiety is, for example, methoxy or ethoxy.

Particular values for certain optional substituents which may be present on a phenyl moiety as $R^1$, or as a part thereof, as defined above, include, for example:

for halogeno: a member selected from the group consisting of fluoro, chloro and bromo;

for (1–4C)alkyl: a member selected from the group consisting of methyl and ethyl; and for (1–4C)alkoxy: a member selected from the group consisting of methoxy and ethoxy.

A particular value for $R^1$ when it is (3–8C)cycloalkyl is, for example, cyclopropyl, cyclobutyl, cyclopentyl, cyclohexyl or cycloheptyl; when $R^1$ is (3–8C)cycloalkyl-(1–6C)alkyl, a particular value is, for example, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl, 1-cyclohexylbutyl; and a particular value for $R^1$ when it is a radical containing an unsaturated linkage in the cycloalkyl ring is, for example, cyclopentenyl, cyclohexenyl, cyclopentyl(1–6C)alkyl (such as cyclopentenylmethyl) or cyclohexenyl-(1–6C)alkyl (such as 1-cyclohexen-4-ylmethyl or 1-(cyclohexenyl)butyl); and a particular value for an optional (1–4C)alkyl substituent on the cyclic moiety of such a radical is, for example, methyl, ethyl or isopropyl.

A particular value for M when it is (1–4C)alkoxycarbonyl is, for example, methoxycarbonyl or ethoxycarbonyl; when it is N-(1–4C)alkylcarbamoyl is, for example, N-methyl- or N-ethylcarbamoyl; when it is N,N-di[(1–C)alkyl]carbamoyl is, for example, N,N-dimethylcarbamoyl; when it is optionally substituted N-phenylcarbamoyl is, for example N-phenylcarbamoyl, N-p-tolycarbamoyl, N-p-chlorophenylcarbamoyl, N-o-tolylcarbamoyl or N-p-anisylcarbamoyl; and when it is (1–6C)alkanoyl is, for example, acetyl, propionyl or butyryl.

Thus, particular values for the radicals include for $R^1$: 1-ethylpentyl, cyclopentyl and cyclpentylmethyl; for $R^2$: hydrogen; for "the other of" $R^3$ or $R^4$: hydrogen, methyl and ethyl, as well as 1-(N,N-dimethylcarbamoyl)ethyl; for Rb: methoxy; for Rc: hydrogen; and for M: hydrogen, cyano and methoxycarbonyl.

More particular values for the groups listed above include by way of example those selected from the groups consisting of:

for $R^1$: ethyl, propyl, isopropyl, butyl, isobutyl, sec-butyl, t-butyl, pentyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, alpha-fluorobenzyl, alpha-methoxybenzyl, cyclobutyl, cyclopentyl, cyclohexyl, cyclopentylmethyl, cyclohexylmethyl, 2-cyclopentylethyl, 1-cyclopentylbutyl, 1-cyclohexylpropyl, 1-cyclohexylbutyl, 5-methyl-2-(1-methylethyl)cyclohexyl and 1-cyclohexen-4-ylmethyl;

for W: oxy, imino, thio and a direct linkage;

for $R^2$: hydrogen, fluoro, chloro, bromo, methyl and methoxy;

for Ra: hydrogen and methyl;

for Rb: hydrogen, methyl and methoxy;

Rc: hydrogen, methyl, methoxy, chloro and bromo;

for Rd: hydrogen, methyl, ethyl, propyl, isopropyl, t-butyl, phenyl, 2-methylphenyl and 4-chlorophenyl;

for Re and Rf (independently selected): hydrogen, methyl and ethyl;

for Rd and Re together with the adjacent nitrogen: piperidine, morpholine, and N-methylpiperazine;

for Rg: methyl, ethyl, propyl, isopropyl, phenyl, 2-methylphenyl and 4-chlorophenyl; and for M: hydrogen, cyano, methoxycarbonyl, ethoxycarbonyl, carbamoyl, N-phenylcarbamoyl, N-methylcarbamoyl, N,N-dimethylcarbamoyl and acetyl.

Examples of specific groups which are of special interest include those selected from the groups consisting of:

for $R^1$: butyl, pentyl, 1-ethylpentyl, 1-phenylpropyl, alpha-fluorobenzyl, alpha-methoxybenzyl, cyclopentyl and cyclopentylmethyl;

for W: oxy, imino and a direct linkage;

for $R^2$: hydrogen;

for Ra: hydrogen;

for Rb: methoxy;

for Rc: hydrogen; and for M: hydrogen and methoxycarbonyl.

A preferred value for $R^1$ when $R^1.L$— is $R^1.W.CO.NH$— and W is an oxy imino is, for example, cyclopentyl; a preferred value for $R^1$ when $R^1.L$— is $R^1.W.CO.NH$— and W is a direct linkage is, for example, 1-ethylpentyl or cyclopentylmethyl; and a preferred value for $R^1$ when $R^1.L$— is $R^1.NH.CO$— is, for example, cyclopentylmethyl.

When the group $R^1.L$ stands for a radical of formula $R^1.NH.CO$—, it is preferred that "the other of $R^3$ and $R^4$" be (1–10C)alkyl optionally containing one or two double or triple bonds and bearing a substituent P.

Two particular groups of compounds of particular interest comprise, for example, the compounds of formulae III and IV:

(Formula set out on pages following Example)   III (Formula set out on pages following Examples)   IV wherein $R^1$, W, A, Rb, Rc and M have any of the meanings defined above and $R^5$ has the same meaning as $R^3$ or $R^4$ apart from a radical of formula II, together with the pharmaceutically acceptable salts thereof.

Specific compounds of the invention are described in the accompanying Examples. However, of those the compound methyl 2-[4-[6-(cyclopentyloxycarbonyl)aminoindazol-1-ylmethyl]-3-methoxybenzoyl]-2-phenylsulphonylacetate is particularly preferred and may be used either in the free aid form or as a corresponding pharmaceutically acceptable salt.

For those compounds of formula I which are sufficiently acidic, examples of suitable pharmaceutically acceptable salts are salts with bases which form a physiologically acceptable cation, such as alkali metal, (especially sodium and potassium), alkaline earth metal (especially calcium and magnesium), aluminum and ammonium salts, as well as salts made with appropriate organic bases such as triethylamine, morpholine, piperidine and triethanolamine. For those compounds of formula I which are sufficiently basic, examples of suitable pharmaceutically acceptable salts include acid-addition salts such as those made with a strong acid, for example, hydrochloric, sulphuric or phosphoric acid.

The compounds of formula I may be made by processes well known in the chemical art for the production of structurally analogous heterocyclic compounds. Such processes for the manufacture of a compound of formula I as defined above are provided as further features of the invention and are illustrated by the following procedures in which the meanings of generic radicals are as defined above; and Hal is defined as halogeno, especially chloro, bromo or iodo.

(A) Reacting a carboxylic acid of formula V:

(Formula set out on pages following Examples)   V wherein $R^6$ and $R^7$ have the meanings defined hereinbefore for $R^3$ and $R^4$ except that the radical of the formula II is replaced by a benzoic acid residue of formula VI:

(Formula set out on pages following Examples)   VI or a reactive derivative thereof, with a sulphone of formula VII:

(Formula set out on pages following Examples)   VII

In general, the sulphone is used preferably in the form of a suitable salt, for example, an alkali metal salts such as the lithium, sodium or potassium salt, which may conveniently be formed in situ by reaction with the appropriate strong base.

A suitable reactive derivative is, for example, an acid halide (such as the chloride), acid cyanide, acid anhydride or a mixed acid anhydride (such as that formed from N,N-diphenylcarbamic acid by reaction of the sodium salt of the acid of formula V with N,N-diphenylcarbamoylpyridinium chloride). In which case, a suitable solvent or diluent such as tetrahydrofuran, methyl t-butyl ether, N,N-dimethylformamide or methylene chloride may conveniently be used at a temperature in the range of, for example, −80° to 20° C.

Alternatively, a free acid of formula V may be used in the presence of a suitable dehydrating agent, for example, dicyclohexylcarbodiimide or 1-(3-dimethylaminopropyl)-3-ethylcarbodiimide (or the hydrochloride or hydrobromide salt thereof), optionally together with a suitable organic base, for example, 4-(dimethylamino)- pyridine. In which case a suitable solvent or diluent such as methylene chloride may conveniently be used at a temperature in the range of, for example, 10° to 50° C., but preferably at or near ambient temperature.

(B) For a compound of formula I wherein $R^1.L—$ stands for a group of formula $R^1.W.CO.NH—$ or $R^1W.CS.NH—$, acylating an amine of formula VIII:

(Formula set out on pages following Examples)  VIII

A suitable acylating agent when W is oxy, thio or a direct link is, for example, an acid halide of formula $R^1.Xa.CO.Hal$ wherein Xa has one of the above-mentioned values for W and Hal is halogeno, especially chloro or bromo.

A suitable acylating agent when W is imino is, for example, an isocyanate of formula $R^1.NCO$.

When an acid halide is used as the acylating agent, a suitable base such as triethylamine, N-methylmorpholine, pyridine or 2,6-lutidine is conveniently also employed, preferably together with a suitable inert solvent or diluent, for example, methylene chloride, diethyl ether, tetrahydrofuran or 1,2-dimethoxyethane. The same or similar inert solvents or diluents may be used when an isocyanate or isothiocyanate is employed as the acylating agent.

When W is a direct link, the acylating agent may also be a carboxylic acid of formula $R^1.CO_2H$. In which case a suitable condensing agent, for example a carbodiimide (such as dicyclohexylcarbodiimide or 1-(3-dimethylaminopropyl)-3-ethylcarbodiimide, or a salt thereof) or 1,1'-carbonyldiimidazole, is also employed, preferably together with a suitable inert solvent or diluent, for example one of those mentioned above for use with an acid halide.

In general, the acylations are carried out at a temperature in the range of, for example, 0°–60° C. and, conveniently, at or near ambient temperature.

Pharmaceutically acceptable salts may be obtained using standard procedures well known in the art, for example, by reacting a sufficiently acidic compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures, for example as illustrated in the Examples.

Thus, for example, a starting amine of formula VIII may be obtained by (i) alkylating an appropriate nitroindole or nitroindazole with the appropriate benzyl halide of formula IX:

(Formula set out on pages following Examples)  IX wherein alkyl has the meaning (1–6C)alkyl, (ii) hydrolysing the resultant ester (for example, using lithium hydroxide), (iii) reacting the resultant carboxylic acid with a sulphone of formula VII, and (iv) catalytically reducing the nitro group to the required amino group.

Similarly, a starting acid of formula V wherein $R^1.L—$ is $R^1.W.CO.NH—$ or $R^1.W.CS.NH—$ may be obtained by (i) alkylating an appropriate nitroindole or nitroindazole with the appropriate benzyl halide of formula IX, (ii) catalytically reducing the nitro group to an amino group, (iii) acylating the amino group using a procedure similar to those described in part (B) above, and (iv) hydrolysing the ester group. As illustrated in the Examples, when $=A—$ is $=C(Ra)—$, alkylation of an appropriate indole at the C(3) position in the preparation of an acid of formula V or an amine of formula VIII may be carried out optionally in the presence of a suitable Lewis acid, such as, for example, silver oxide; and alkylation at the N(1) position in the preparation of an acid of formula V or an amine of formula VIII may be carried out preferably in the presence of a suitable base, for example, potassium carbonate or sodium hydride in an appropriate solvent; or a preformed anhydrous alkali metal salt at N(1) may be employed. Alternatively, when $=A—$ is $=N—$, selective positioning of the substituted benzyl group at the N(1) position may be achieved by (i) chlorinating a nitroindazole of formula X:

(Formula set out on pages following Examples)  X wherein $R^8$ has the value hydrogen, (ii) alkylating the resulting compound of formula X wherein $R^8$ has the value chloro (conveniently isolated and used as its sodium salt) with the appropriate benzyl halide of formula IX to obtain a compound of formula XI:

(Formula set out on pages following Examples)  XI (iii) catalytically hydrogenating the resulting compound of formula XI to afford an amine of formula XII:

(Formula set out on pages following Examples)  XII (iv) acylating the amino group of the amine of formula XII using a procedure similar to those described in part (B) above, and (v) hydrolysing the ester group of the resulting compound to give the acid starting material of the formula V, for example, as described in Example 5. In addition, when $=A—$ is $=N—$, selective positioning of the benzyl group at the C(3) position may be achieved by (i) cross coupling a nitroindazole of formula XIII:

(Formula set out on pages following Examples)  XIII with an appropriate benzyl halide, such as a compound of formula IX, by, for example, using a stoichiometric amount of activated zinc dust and a catalytic quantity of a transition metal catalyst, such as, for example, dichloro[1,1'-bis(diphenylphosphino)ferrocene]palladium(II) or dichlorobis(triphenylphosphine)nickel(II); (ii) catalytically reducing the nitro group of the resulting compound to afford an amine of formula XIV:

(Formula set out on pages following Examples)  XIV (iii) acylating the amino group of the amine of formula XIV using a similar procedure to that described in part (B) above; and (iv) hydrolysing the ester group of the resulting compound to give an acid starting material of formula V.

A starting acid of formula V wherein $R^1.L—$ is $R^1.NH.CO—$ may be made by analogous methods to those discussed above by starting with the corresponding carboxyindole or carboxyindazole (or its ester) and an amine of formula $R^1.NH_2$ and using a standard coupling method to form an indolecarboxamide or indazolecarboxamide, followed by substitution at the N(1) and C(3) positions, for example, as described in Example 13.

A further method for preparing a starting acid of formula V involves (i) conversion of an indole compound of formula XV:

(Formula set out on pages following Examples)     XV wherein $=A-$ is $=C(Ra)-$ and $R^9$ and $R^{10}$ have the meanings defined hereinabove for $R^3$ and $R^4$ except that the radical of formula II is replaced by a benzoic ester residue of formula XVI:

(Formula set out on pages following Examples)     XVI into a corresponding indazole ester of formula XV, wherein $=A-$ is $=N-$, followed by (ii) hydrolysis of the ester group. The conversion may be carried out by (i) oxidatively cleaving the 2,3-double bond of the indole using techniques known in the art, (ii) converting the resulting ketone of formula XVII:

(Formula set out on pages following Examples)     XVII into the oxime of formula XVIII:

(Formula set out on pages following Examples)     XVIII using standard procedures known in the art, and (iii) dehydrating the oxime of formula XVIII to provide the indazole ester of formula XV, wherein $=A-$ is $=N-$, by using an appropriate method, such as, for example, heating directly or after prior derivitization to the corresponding O-acyloxime with a suitable reagent, such as, for example, acetic anhydride, for example as described in Example 9.

As stated previously, the compounds of formula I possess leukotriene antagonist properties. Thus, they antagonise the actions of one or more of the arachidonic acid metabolites known as leukotrienes, for example, $C_4$, $D_4$, and/or $E_4$, which are known to be powerful spasmogens (particularly in the lung), to increase vascular permeability and have been implicated in the pathogenesis of asthma and inflammation (see J. L. Marx, Science, 1982, 215, 1380–1383) as well as of endotoxic shock (see J. A Cook, et al., J. Pharmacol. Exp. Ther., 1985, 235, 470) and traumatic shock (see C. Denzlinger, et al., Science, 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, and psoriasis, as well as vasospastic cardiovascular disease and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I generally may be administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained by employing conventional procedures and using excipients and binders and may be administered in a variety of dosage forms. For example, the compositions may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose compound of formula I to be administered will necessarily be varied according to principles well known in the art taking account of the route of administration, the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (J. Pharmacol. Exp. Ther. 1979, 211, 436). Using this procedure, tracheal tissue strips are set up in groups of eight, four being used as time/vehicle (dimethyl sulfoxide) controls and four for each test compound. All of the strips are exposed to $8 \times 10^{-9}$M leukotriene $E_4(LTE_4)$ following the 50 minute equilibration period, and the response is recorded. This $8 \times 10^{-9}$M concentration of $LTE_4$ is that which produces a contraction equal to about 70–80% of the maximal effect of the agonist in this tissue. The $LTE_4$ is washed out for 40–45 minutes and the procedure is repeated twice to ensure that reproducible responses are being obtained with $LTE_4$. Leukotriene $C_4(LTC_4)$ or $D_4(LTD_4)$, at a concentration of $8 \times 10^{-9}$M, may be substituted for $LTE_4$ in the same procedure.

Once tissue reproducibility has been established, test compounds are added to four baths following the 40–45 minute washout period. After a 10 minute incubation with test compound or vehicle, $8 \times 10^{-9}$M $LTE_4$, $LTD_4$ or $LTC_4$ is added and the response recorded. The percentage inhibition by the test compound or the percentage change in vehicle controls is calculated, for each tissue, according to the following equation: % inhibition=100 multiplied by (mg tension increase of preceding response minus mg tension increase in presence of compound) divided by mg tension increase of preceding response. The mean percentage change for vehicle controls and test compound are calculated and evaluated for significant differences by Student's t-test for unpaired data. Tissues exposed to test compounds are retested for responsiveness to LTE$_4$, LTD$_4$ or LTC$_4$ following a 45 minute washout period. If tissue responsiveness is equal to responsiveness preceding exposure to the test compound additional studies are conducted. If responsiveness is not restored by the washing procedure, the tissues are discarded. The cyclooxygenase inhibitor, indomethacin, is present at $5\times10^{-6}$M in all the determinations.

In general, the compounds of formula I tested demonstrated statistically significant activity as LTC$_4$, LTD$_4$ and/or LTE$_4$ antagonists in the above test at a concentration of about $10^{-5}$M or much less.

The selectivity of action of these compounds as leukotriene antagonists as opposed to non-specific smooth muscle depressants may be shown by carrying out the above in vitro procedure using the non-specific spasmogen barium chloride at a concentration of $1.5\times10^{-3}$M, again in the presence of indomethacin at $5\times10^{-6}$M.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene LTD$_4$ (starting with 3 ml of a 30 microgram/ml solution) and the effect of the test compound on the average time of leukotriene initiated change in breathing pattern (such as onset of dyspnoea) recorded and compared with that in undosed, control guinea-pigs. In general, compounds of formula I tested produced a significant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) all operations were carried out at room or ambient temperature, that is, at a temperature in the range of 18°-25° C.;

(ii) evaporation of solvent was carried out using a rotary evaporator under reduced pressure (600-4000 pascals; 4.5-30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz or 250 MHz using CDCl$_3$, DMSO-d$_6$ or CD$_3$OD as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: v (volume), w (weight); mp (melting point), l [liter(s)], ml (milliliters), g [gram(s)], mg [milligram(s)]; and (xi) some compounds are denoted by letters, for example (A), for later reference in the Examples.

EXAMPLE 1

6-(2-Ethylhexanamido)-1-[2-methoxy-4-[2-(phenylsulphonyl)acetyl]benzyl]indole

A solution of butyllithium (0.86 ml of a 2.3M solution in hexanes) was added to a solution of methyl phenyl sulphone (312 mg) in dry tetrahydrofuran (THF) (5 ml.) at $-78°$ C. After 15 minutes a white suspension formed. To this mixture was then added a solution of 4-[6-(2-ethylhexanamido)indole-1-yl-methyl]-3-methoxybenzoic N,N-diphenylcarbamic anhydride (A) (500 mg) in THF (4 ml). After two hours, the mixture was allowed to warm to ambient temperature and an excess of a saturated solution of potassium dihydrogen phosphate was added. The solvent was removed by evaporation and the residue was partitioned between water and ethyl acetate. The organic phase was dried (Na$_2$SO$_4$) and evaporated. The residual gum was purified by chromatography on silica gel (20 g), using 2:98 v/v ether:methylene chloride as eluent, to give the title compound as a white solid (200 mg, 44%); mp 131°-133° C.

Analysis calculated for C$_{32}$H$_{36}$N$_2$O$_5$S: C, 68.5; H, 6.47; N, 5.0. Found: C, 68.28; H, 6.53; N, 4.98.

The starting material (A) was obtained as follows:

(a) A solution of 3-methoxy-4-methylbenzoic acid (6.0 g) in methanol (120 ml) was treated with acetyl chloride (6 ml) and stirred for 36 hours. The solution was evaporated. The residue was dissolved in methanol (100 ml) and the solution evaporated. This procedure was repeated to give methyl 3-methoxy-4-methylbenzoate as a colorless oil (6.34 g, 98%); NMR: 2.2(s, 3H, CH$_3$), 3.9(2s, 6H, 2xOCH$_3$), 7.1(d, 1H), 7.5(m, 2H). A solution of ester prepared according to the method described above (121.2 g) in carbon tetrachloride (1400 ml) was heated under gentle reflux with a 350 watt tungsten lamp and subjected to an air purge by means of a T-tube attached to a water aspirator. A solution of bromine (107.2 g) in carbon tetrachloride (500 ml) was added dropwise over 4 hours. Evaporation of the solvent gave a light yellow solid which was triturated with a solution (500 ml) of 1:9 (v/v) ether:hexane. The solid was collected by filtration to give methyl 4-bromomethyl-3-methoxybenzoate (111.7 g, 64%) as a light yellow solid; mp 87°-90° C.; NMR: 3.9(2s, 6H, 2xOCH$_3$), 4.5(s, 2H, BrCH$_2$), 7.4(m, 3H).

(b) A solution of 6-nitroindole (4.0 g) and methyl 4-bromomethyl-3-methoxybenzoate (6.71 g) in dry acetone (125 ml) was treated with anhydrous potassium carbonate (4.0 g). The mixture was heated under reflux for 48 hours. The cloudy mixture was evaporated. The residue was suspended in ethyl acetate, and solid removed by filtration. The filtrate was evaporated and the residual oil was purified by flash chromatography on a 6×30 cm column of silica gel using 1:1 (v/v) methylene chloride:hexane as the eluent to give methyl 3-methoxy-4-(6-nitroindol-1-ylmethyl)benzoate as a bright yellow powder (8.0 g); NMR: 3.9(s, 3H, OCH$_3$), 4.0(s, 3H, OCH$_3$), 5.4(s, 2H, NCH$_2$), 6.7(dd, 1H, H$^3$-indole), 6.8(d, 1H), 7.4(d, 1H, H$^2$-indole), 7.5-7.7(m, 3H), 8.0(dd, 1H, H$^5$-indole), 8.3(br s, 1H, H$^7$-indole). A solution of a portion of the above nitroester (1.38 g) in ethyl acetate (15 ml), which contained 2 drops of 1:4 (v/v) acetic acid:ethyl acetate, was added to a suspension of prereduced 10% w/w palladium-on-charcoal (0.34 g) in ethyl acetate (5 ml). The mixture was shaken under 3.45 bar hydrogen for 24 hours and then filtered through diatomaceous earth. The residue was washed with hot chloroform and the combined filtrate and washings were evaporated to give methyl 4-(6-aminoindol-1-ylmethyl)-3-methoxybenzoate (B) (1.19 g) as a brown powder; NMR: 3.6(br, 2H, NH$_2$), 3.9(s, 3H, OCH$_3$), 4.0(s, 3H, OCH$_3$), 5.3(s, 2H, NCH$_2$), 6.4(d, 1H, H$^3$-indole), 6.5(s, 1H, H$^7$-indole), 6.6(m, 2H), 6.9(d, 2H, H$^2$-indole), 7.5(m, 3H).

(c) A stirred solution of methyl ester (B) (0.5 g) in methylene chloride (16 ml) was cooled to 0° C. and treated with triethylamine (0.34 ml) followed by 2-ethylhexanoyl chloride (0.31 ml). The resulting solution was stirred at 0° C. for 15 minutes and then at room temperature for 30 minutes. The mixture was diluted with ethyl acetate and poured into cold water. The organic layer was washed sequentially with 10% v/v hydrochloric acid, water, and brine; dried (MgSO$_4$) and evaporated. The residue was purified by flash chromatography on a 4×18 cm silica gel column using 35:65 v/v ethyl acetate:hexane as the eluent to give methyl 4-[6-(2-ethylhexanamido)indol-1-ylmethyl]-3-methoxybenzoate (C) (0.7 g; 99%) as a white solid; partial NMR: 0.9(t, 6H, 2CH$_3$), 1.5(m, 9H).

(d) A mixture of ester (C) (0.7 g), lithium hydroxide hydrate (0.41 g), tetrahydrofuran (4 ml), methanol (4 ml), and water (1.6 ml) was stirred overnight. The mixture was then evaporated. The white solid obtained was dissolved in water (50 ml). Acidification of this homogeneous alkaline solution by dropwise addition of 10% v/v hydrochloric acid gave a fine white precipitate which was recrystallized from ethyl acetate (40 ml) to give 4-[6-(2-ethylhexanamido)indol-1-ylmethyl]-3-methoxybenzoic acid (D) (0.13 g; 30%) as a solid; mp 234°-235° C.

(e) A solution of the acid (D) (3.1 g) and triethylamine (1.0 ml) in methanol (30 ml) was treated with a solution of N,N-diphenylcarbamoylpyridinium chloride (2.5 g) in methanol (30 ml). The resultant precipitate was collected by filtration, washed with methanol, and dried under vacuum to give 4-[6-(2-ethylhexanamido)indol-1-ylmethyl]-3-methoxybenzoic N,N-diphenylcarbamic anhydride (A) as a white solid (3.54 g, 79%); mp 159°-162° C.

Analysis calculated for: C$_{38}$H$_{39}$N$_3$O$_5$: C, 73.88; H, 6.36; N, 6.80. Found: C, 73.77; H, 6.37; N, 6.67.

EXAMPLE 2

Methyl 2-[4-[6-(2-ethylhexanamido)indol-1-ylmethyl]-3-methoxybenzoyl]-2-phenylsulphonylacetate A solution of lithium diisopropylamide (6.0 ml of a 0.5M solution in THF) was added to a solution of methyl 2-(phenylsulphonyl)acetate (650 mg) in THF (5.0 ml) at −78° C. A solution of 4-[6-(2-ethylhexanamido)indol-1-ylmethyl]-3-methoxybenzoic N,N-diphenylcarbamic anhydride (A) (617 mg) in THF (5.0 ml) was added to the resultant mixture. After 2 hours, the reaction solution was allowed to warm to room temperature overnight and an excess of a solution of potassium dihydrogen phosphate was then added. The solvent was evaporated and the residue partitioned between water and ethyl acetate. The organic phase was separated, dried (Na$_2$SO$_4$) and evaporated. The resultant yellow oil was purified by chromatography on silica gel (42 g) using an increasing gradient of ether:methylene chloride (up to 1:19 v/v ether:methylene chloride). The title compound was thus obtained as an oil which was crystallized by treatment with methyl t-butyl ether to give an off-white solid (172 mg, 17%); mp 148°-149° C.

Analysis calculated for C$_{34}$H$_{38}$N$_2$O$_7$S: C, 66.0; H, 6.19; N, 4.52. Found: C, 65.86; H, 6.29; N, 4.55.

EXAMPLE 3

2-[4-[6-(2-Ethylhexanamido)indol-1-ylmethyl]-3-methoxybenzoyl]-2-phenylsulphonylacetonitrile Using a procedure similar to Example 2, but using (phenylsulfonyl)acetonitrile instead of methyl 2-(phenylsulphonyl)acetate and by using ethyl acetate:chloroform instead of ether:methylene chloride as eluent, the title compound was obtained as an offwhite powder; mp 184° C. (dec), hydrate.

EXAMPLE 4

Methyl 2-[4-[5-(2-cyclopentylacetamido)-1-ethylindol-3-ylmethyl]-3-methoxybenzoyl]-2-phenylsulfonylacetate A solution of potassium bis(trimethylsilyl)amide (7.1 ml of a 0.8M solution in toluene) was added to a solution of methyl 2-(phenylsulfonyl)acetate (1.24 g) in tetrahydrofuran (THF) (9.0 ml) at −78° C. This mixture was then added to a solution of 4-[5-(2-cyclopentylacetamido)-1-ethylindol-3-ylmethyl]-3-methoxybenzoic N,N-diphenylcarbamic anhydride (E) (600 mg) in THF at −78° C. The reaction solution was allowed to warm to room temperature overnight and saturated potassium dihydrogen phosphate (20 ml) was then added. The mixture was made acidic to pH 4 with the addition of 1N HCl and partitioned with ethyl acetate. The organic layer was washed with water and saturated brine, dried (MgSO$_4$) and evaporated. The residue was purified by chromatography on silica gel (41 g) using chloroform as the eluent. The title compound was obtained as an oil which was crystallized from methyl t-butyl ether/hexane to give a pale yellow solid (64.5 mg, 10%); mp 78°-80° C.

Analysis calculated for C$_{35}$H$_{38}$N$_2$O$_7$S.0.25H$_2$O.0.25 methyl t-butyl ether: C, 66.24; H, 6.36; N, 4.26. Found: C, 66.27; H, 6.57; N, 4.13.

The mixed anhydride (E) was obtained by procedures similar to the following:

(a) Silver(I) oxide (7.15 g) was added to a solution of 5-nitroindole (5 g) and methyl 4-bromomethyl-3-methoxybenzoate (prepared as described in step (a) of Example 1) (7.99 g) in dioxane (30 ml), under a nitrogen atmosphere. The mixture was stirred at 60° C. for 20 hours, dioxane removed by evaporation, and ethyl acetate (50 ml) added to the residue. The resulting suspension was separated by filtration through diatomaceous earth. The filtrate was evaporated to give a dark viscous oil, which was purified by flash chromatography on silica gel (600 ml), eluting with 3:7 v/v ethyl acetate:hexane. The viscous yellow oil obtained was crystalized from a mixture of methylene chloride and hexane to give methyl 3-methoxy-4-(5-nitroindol-3-ylmethyl)-benzoate (F) (4.6 g, 45%) as yellow needles; mp 153°–155° C.; NMR: 3.83(s, 3H, COOCH$_3$), 3.93(s, 3H, OCH$_3$), 4.12(s, 2H, CH$_2$Ar), 7.25(d, 1H), 7.43(d, 1H), 7.49(m, 3H), 7.95(dd, 1H, H$^6$-indole), 8.47(d, 1H, H$^4$-indole), 11.65(broad s, 1H, H$^1$-indole).

(b) Methyl 3-methoxy-4-(5-nitroindol-3-ylmethyl)-benzoate (F) (5.30 g) was added to a stirred suspension of oil-free sodium hydride (0.424 g) in dry N,N-dimethylformamide (25 ml), under an atmosphere of nitrogen. The dark-red solution was stirred for 15 minutes, and iodoethane (3.04 g) was added. The mixture was stirred for 30 minutes, and was poured into 1M hydrochloric acid (75 ml). The mixture obtained was extracted with ethyl acetate (2×50 ml). The combined extracts were washed with brine (25 ml), then dried (MgSO$_4$), and evaporated. The yellow oil obtained was purified by flash chromatography on silica gel (600 ml), eluting with 70:30 v/v hexane:ethyl acetate, to give methyl 3-methoxy-4-(1-ethyl-5-nitroindol-3-ylmethyl)-benzoate (G) as a yellow oil, which was crystallized from methylene chloride/hexane to give yellow needles (4.88 g, 82%); mp 129°–30° C.; 1.34(t, 3H, CH$_2$CH$_3$), 3.83(s, 3H, CO.OCH$_3$), 3.92(s, 3H, OCH$_3$), 4.11 (s, 2H, CH$_2$Ar), 4.23(q, 2H, CH$_2$CH$_3$), 7.27(d, 1H), 7.48(m, 2H), 7.64(d, 1H), 7.99(dd, 1H, H$^6$-indole), 8.49(d, 1H, H$^4$-indole).

(c) A solution of ester (G) (4.80 g) in tetrahydrofuran (75 ml) was hydrogenated in the presence of palladium-on-carbon (10% w/w; 0.25 g), at 3.45 bar for 2 hours. The catalyst was removed by filtration through diatomaceous earth and the filtrate was evaporated. The residual oil was purified by flash chromatography to give methyl 4-(5-amino-1-ethylindol-3-ylmethyl)-3-methoxybenzoate (H) as an amber oil (4.43 g, 100%); TLC, silica gel, R$_f$=0.23, hexane:ethyl acetate (6:4 v/v).

(d) A mixture of the ester (H) described above (used without further characterization) (4.43 g), cyclopentylacetic acid (1.85 g), 4-(dimethylamino)pyridine (1.76 g), and 1-(3-dimethylaminopropyl)-3-ethylcarbodiimide hydrochloride (3.26 g), was dissolved in methylene chloride (100 ml), under an atmosphere of nitrogen, and stirred at room temperature for 18 hours. The mixture was poured into 1M hydrochloric acid (25 ml), the separated aqueous layer extracted with dichloromethane (2×100 ml), the combined organic extracts washed with water, brine, dried (MgSO$_4$) and evaporated. The residual oil was crystallized from ethanol to give off-white needles which were recrystallized from methylene chloride/hexane to give methyl 4-[5-(2-cyclopentylacetamido)-1-ethylindol-3-ylmethyl]-3-methoxybenzoate (I) as a white powder (5.12 g, 87%); mp 144°–146° C.; partial NMR (250 MHz, DMSO-d$_6$): 1.17(m, 2H), 1.32(t, 3H), 1.4–1.8(m, 6H), 2.25(m, 3H), 3.82(s, 3H, OCH$_3$), 3.92(s, 3H, OCH$_3$), 3.97 (s, 2H, ArCH$_2$), 4.09(q, 2H, CH$_2$CH$_3$), 9.61(s, 1H, NH).

(e) Using a similar procedure to that described in part (d) of Example 1, the ester (I) was converted into 4-[5-(2-cyclopentylacetamido)-1-ethylindol-3-ylmethyl]-3-methoxybenzoic acid (J), obtained as a solid (83%); mp 219°–220° C.

(f) A solution of N,N-diphenylcarbamoylpyridinium chloride (311 mg) in methanol (1 ml) was added to a stirred solution of the acid (J) (450 mg) and sodium hydroxide (1 ml of a 1M aqueous solution) in methanol (4 ml) under an atmosphere of nitrogen. After stirring for 1.5 minutes, ethyl acetate and N,N-dimethylformamide (2 ml) were added and the mixture allowed to stir until all dissolved. The ethyl acetate solution was washed with water and saturated brine, dried (MgSO$_4$) and evaporated to give a quantitative yield of 4-[5-(2-cyclopentylacetamido)-1-ethylindol-3-ylmethyl]-3-methoxybenzoic N,N-diphenylcarbamic anhydride (E) as a crusty foam; partial NMR: (80 MHz, DMSO-d$_6$): 1.30(t, J=7.1 Hz, 2H, NCH$_2$CH$_3$), 3.84(s, 3H, OCH$_3$), 3.94(s, 2H, ArCH$_2$), 4.05(q, J=7.1 Hz, 2H, NCH$_2$CH$_3$), 7.41(s, 10H, NArH), 9.56(s, 1H, CONH).

EXAMPLE 5

Methyl 2-[4-[6-(cyclopentyloxycarbonyl)aminoindazol-1-ylmethyl]-3-methoxybenzoyl]-2-phenylsulphonylacetate Using a procedure similar to that of Example 4, but using 4-[6-(cyclopentyloxycarbonyl)aminoindazol-1-ylmethyl]-3-methoxybenzoic N,N-diphenylcarbamic anhydride (K) instead of anhydride (E) and by using chloroform then 2:98 v/v acetonitrile:chloroform instead of chloroform as eluent, the title compound was obtained as a white powder (150 mg, 38%); mp 76°–78° C.

The mixed anhydride (K) was obtained as follows:

(a) To a mixture of 6-nitroindazole (1.63 g) and 6N sodium hydroxide (2.08 ml) was added 5.25% w/v sodium hypochlorite (17.86 ml). After stirring for 30 minutes, filtration, and washing with 1N sodium hydroxide, 1-sodio-3-chloro-6-nitroindazole (2.08 g, 95%) was obtained as a solid; mp >270° C.

(b) To a mixture of the sodium salt (2.19 g) (obtained as described in part (a) above) in methanol (50 ml) was added methyl 3-methoxy-4-bromomethylbenzoate (obtained as described in part (a) of Example 1) (2.85 g) in methanol (50 ml), and the mixture was stirred for 2 hours. After the addition of water (150 ml), the resulting precipitate was filtered and recrystallized from hot ethyl acetate to give methyl 4-[3-chloro-6-nitroindazol-1-ylmethyl]-3-methoxybenzoate (2.63 g, 70%) as a solid; mp 167.0°–167.5° C.

(c) A mixture of the product of part (b) above (1.25 g) and palladium on calcium carbonate (385 mg, 3.65 mmol of CaCO$_3$) in 1:1 v/v methanol:ethyl acetate (40 ml) was hydrogenated at 1.1 bar for 3 hours. After filtration through diatomaceous earth, evaporation to about 3 ml of solution, and crystallization from petroleum ether and ethyl ether at −20° C., methyl 4-(6-aminoindazol-1-ylmethyl)benzoate (L) (930 mg, 90%) was obtained as a solid; mp 131.0°–131.5° C.

(d) To a mixture of indazole (L) (150 mg), pyridine (0.05 ml) and methylene chloride (2 ml), at −20° C., was added cyclopentyl chloroformate (0.07 ml). The reaction was warmed to 25° C. and stirred for 1 hour. The reaction mixture was added to ethyl acetate, and the ethyl acetate solution washed with saturated sodium carbonate, 1N HCl, and brine, and dried (MgSO$_4$). Evaporation and trituration with diethyl ether gave methyl 4-[6-(cyclopentyloxycarbonyl)aminoindazol-1-ylmethyl]-3-methoxybenzoate (M) (148 mg, 73%) as a solid; mp 150.0°–151.0° C.

Analysis calculated for $C_{23}H_{25}N_3O_5$: C, 65.24; H, 5.95; N, 9.92. Found: C, 65.05; H, 5.95; N, 9.47.

(e) Using a similar procedure to that described in part (d) of Example 1, the ester (M) was converted into 4-[6-(cyclopentyloxycarbonyl)aminoindazol-1-ylmethyl]-3-methoxybenzoic acid (N) (39%) as a solid; mp 235°–236.5° C.

(f) Using a procedure similar to part (f) of Example 4, but using 4-[6-(cyclopentyloxycarbonyl)aminoindazol-1-ylmethyl]-3-methoxybenzoic acid (N) instead of acid (J), there was obtained 4-[6-(cyclopentyloxycarbonyl)aminoindazol-1-ylmethyl]-3-methoxybenzoic N,N-diphenylcarbamic anhydride (K) as a pink solid (2.14 g, 96%); partial NMR: (80 MHz, DMSO-$d_6$): 3.86(s, 3H, OCH3), 5.49(s, 2H, ArCH$_2$N), 7.42(s, 10H, NArH), 9.69(s, 1H, CONH).

EXAMPLE 6

Methyl 2-[4-[6-(2-cyclopentylacetamido)indol-1-ylmethyl]-3-methoxybenzoyl]-2-phenylsulfonylacetate Using a procedure similar to Example 2, but using 4-[6-(2-cyclopentylacetamido)indol-1-ylmethyl]-3-methoxybenzoic N,N-diphenylcarbamic anhydride (O) instead of anhydride (A), the title compound was obtained (63 mg, 9.5%) as an off-white solid; mp 93°–98° C.

Analysis calculated for $C_{33}H_{34}N_2O_7S$: C, 65.76; H, 5.68; N, 4.67. Found: C, 65.60; H, 6.05; N, 4.34.

The mixed anhydride (O) was obtained as follows:

(a) A solution of cyclopentylacetic acid (0.24 ml) and 1,1'-carbonyldiimidazole (0.34 g) in methylene chloride (3 ml) was heated under reflux for 30 minutes and then treated with a solution of ester (B) (0.5 g) in methylene chloride (3 ml). The mixture was heated under reflux for 30 minutes, stirred at room temperature for 24 hours, and then diluted with ethyl acetate. This organic solution was washed sequentially with 10% v/v hydrochloric acid, water, and brine, dried (MgSO$_4$) and evaporated. The residue was purified by flash chromatography on a 6×18 cm silica gel column using 99:1 v/v ethyl acetate:toluene as the eluent followed by recrystallization from hexane/ethyl acetate to give methyl 4-[6-(2-cyclopentylacetamido)indol-1-ylmethyl]-3-methoxybenzoate (P) as a solid; partial NMR: 2.0–2.5(br m, 3H, CH$_2$CH), 3.9(s, 3H, OCH$_3$), 4.0(s, 3H, OCH$_3$), 5.3(s, 2H, NCH$_2$).

(b) The above ester (P) was hydrolyzed according to the procedure of Example 1d to give a 35% yield of 4-[6-(2-cyclopentylacetamido)indol-1-ylmethyl]-3-methoxybenzoic acid (Q) as a solid; mp 259°–260° C.

(c) Using a procedure similar to part (f) of Example 4, but using 4-[6-(2-cyclopentylacetamido)indol-1-ylmethyl]-3-methoxybenzoic acid (Q) instead of acid (J), there was obtained 4-[6-(2-cyclopentylacetamido)indol-1-ylmethyl]-3-methoxybenzoic N,N-diphenyl carbamic anhydride (O) as an off-white powder (1.4 g, 92%); partial NMR: (80 MHz, DMSO-$d_6$): 3.98(s, 3H, OCH3) 5.30(s, 2H, NCH$_2$Ar), 7.40(s, 10H, NArH), 9.69(s, 1H, CONH).

EXAMPLE 7

5-(Cyclopentyloxycarbonyl)amino-3-[2-methoxy-4-[2-[(2-methylphenyl)sulphonyl]acetyl]benzyl-1-methylindole Using a similar procedure to that described in Example 1, but using methyl 2-methylphenyl sulphone instead of methyl phenyl sulphone and using 4-[5-(cyclopentyloxycarbonyl)amino-1-methylindole-3-ylmethyl]-3-methoxybenzoic N,N-diphenylcarbamic anhydride (R') instead of anhydride (A), the title compound was obtained as a yellow powder; mp 85°–90° C.

Analysis calculated for $C_{32}H_{34}N_2O_6S.1.0H_2O$: C, 64.84; H, 6.12; N, 4.72. Found: C, 65.00; H, 5.83; N, 4.46.

The starting material (R') was obtained as follows:

(a) Methyl 3-methoxy-4-(5-nitroindol-3-ylmethyl)benzoate (F) (0.44 g) was added to a stirred suspension of oil-free sodium hydride (0.31 g) in dry tetrahydrofuran (10 ml), under an atmosphere of nitrogen. The dark-red solution was stirred for 10 minutes, and iodomethane (0.18 g) was added. The mixture was stirred for 30 minutes, and was poured into 1M hydrochloric acid (30 ml). The mixture obtained was extracted with ethyl acetate (2×50 ml). The combined extracts were washed with brine (25 ml), then dried (MgSO$_4$), and evaporated. The yellow oil obtained was purified by flash chromatography on silica gel (50 ml), eluting with 50:45:5 v/v/v hexane:dichloromethane:ethyl acetate, to give methyl 3-methoxy-4-(1-methyl-5-nitroindol-3-ylmethyl)benzoate (F') (0.33 g, 72%) as a yellow oil, which was crystallized from dichloromethane/hexane to give a yellow solid, mp 144°–146° C.; NMR: 3.81(s, 3H, NCH$_3$), 3.83(s, 3H, COOCH$_3$), 3.92(s, 3H, OCH$_3$), 4.11(s, 2H, CH$_2$Ar), 7.27(d, 1H), 7.37(s, 1H, H$^2$-indole), 7.49 (m, 2H), 7.60(d, 1H), 8.01(dd, 1H, H$^6$-indole), 8.50(d, 1H, H$^4$-indole).

(b) A solution of (F') (0.56 g) in tetrahydrofuran (30 ml) was hydrogenated in the presence of palladium-on-carbon (10% w/w; 0.1 g), as described for the amino ester (H) in Example 4, to give methyl 4-(5-amino-1-methylindol-3-ylmethyl)-3-methoxybenzoate (S) (0.50 g, 98%) as pale yellow foam; NMR: 3.6(s, 3H, NCH$_3$), 3.8(s, 3H, COOCH$_3$), 3.9(br s, 5H, OCH$_3$ and CH$_2$Ar), 4.45(br, 2H, NH$_2$), 6.54(m, 2H), 6.86(s, 1H), 7.04(m, 2H), 7.40(m, 2H).

(c) Cyclopentyl chloroformate (0.11 g) was added to a stirred solution of methyl 4-(5-amino-1-methylindol-3-ylmethyl)-3-methoxybenzoate (S) (0.25 g) and N-methylmorpholine (0.23 g) in dichloromethane (3 ml), under an atmosphere of nitrogen. The mixture was stirred for 2 hours and then poured into 1M hydrochloric acid (20 ml). This acid mixture was extracted with ethyl acetate (2×30 ml). The combined extracts were washed with saturated brine (20 ml), dried (MgSO$_4$), and evaporated to give a viscous oil. This was purified by flash chromatography on silica gel (50 ml), eluting with 3:7 v/v ethyl acetate:hexane, to give methyl 4-[5-(cyclopentyloxycarbonyl)amino-1-methyl-indol-3-ylmethyl]-3-methoxybenzoate (T) as a foam (0.25 g, 74%); NMR: 1.62[m, 8H, (CH$_2$)$_4$], 3.68(s, 3H, NCH$_3$), 3.83(s, 3H, COOCH$_3$), 3.91(s, 3H, OCH$_3$), 3.95(s, 2H, CH$_2$Ar), 5.05(m, 1H, —CHO—), 7.11(m, 2H), 7.26(d, 1H), 7.43 (m, 2H), 7.59(br, 1H), 9.18 (br, 1H, NH).

(d) Using a similar procedure to that of part (d) of Example 1, the ester (T) was converted into 4-[5-(cyclopentyloxycarbonyl)amino-1-methylindol-3-ylmethyl]-3-methoxybenzoic acid (R), obtained as a white solid (88%); mp 157°–158° C.

Using a similar procedure to that described in part (f) of Example 4, the acid (R) was converted into 4-[5-(cyclopentyloxycarboryl)amino-1-methylindol-3-ylmethyl]-3-methoxybenzoic N,N-diphenylcarbamic anhydride (R') as a crusty foam; partial NMR: (80 MHz, DMSO-$d_6$): 3.67(s, 3H, NCH$_3$), 3.84(s, 3H, OCH$_3$), 3.92(s, 2H, ArCH$_2$), 5.02(m, 1H, OCH(CH$_2$)$_4$), 9.14(s, 1H, CONH).

EXAMPLE 8

Methyl 2-[4-[5-(Cyclopentyloxycarbonyl)amino-1-methylindol-3-ylmethyl]-3-methoxybenzoyl]-2-phenylsulphonylacetate Using a similar procedure to that described in Example 4 but using 4-[5-(cyclopentyloxycarbonyl)amino-1-methylindol-3-ylmethyl]-3-methoxybenzoic N,N-diphenylcarbamic anhydride (R') in place of the anhydride (E), the title compound was obtained as a white powder; mp 65°–70° C.; partial NMR: (250 MHz, CDCl$_3$): 3.72(s, 3H, NCH$_3$), 3.73(s, 3H, OCH$_3$), 3.94(s, 3H, OCH$_3$), 4.08(s, 2H, ArCH$_2$), 5.20(m, 1H, OCH(CH$_2$)$_4$), 5.98(s, 1H, —COCH(CO$_2$—)SO$_2$Ar) 6.5(br s, 1H, ArNHCO$_2$—), 6.8(s, 1H, —NCH=C).

Analysis calculated for C$_{33}$H$_{34}$N$_2$O$_8$S.0.5H$_2$O: C, 63.14; H, 5.61; N, 4.46. Found: C, 63.00; H, 5.83; N, 4.53.

EXAMPLE 9

5-(Cyclopentyloxycarbonyl)amino-3-[2-methoxy-4-[2-(phenylsulphonyl)acetyl]benzyl]-1-methylindazole Using a similar procedure to that of part (f) of Example 4 but using 4-[5-(cyclopentyloxycarbonyl)amino-1-methylindazol-3-ylmethyl]-3-methoxybenzoic acid (U) in place of the acid (J) to form a mixed anhydride and by using a similar procedure to that described in Example 1 but using the anhydride so formed in place of the anhydride (A), the title compound may be prepared.

The starting material (U) was obtained as follows:

(a) Rose Bengal (0.025 g) was added to a solution of methyl 4-[5-(cyclopentyloxycarbonyl)amino-1-methylindol-3-ylmethyl]-3-methoxybenzoate (T) (2.0 g) in dry methanol (200 ml). The resulting red solution was introduced, together with a magnetic stirring bar, into a quartz photolysis apparatus fitted with a gas bubbler, drying-tube, and a water-cooled immersion tube housing a quartz tungsten-halogen lamp (type DVY, 650 watts). Purified, dry oxygen gas was bubbled through the stirred solution while irradiating the solution. After 1.5 hours (TLC monitoring), the methanol solution was removed from the apparatus, evaporated, and filtered through a column of silica gel (6 cm diameter column) eluting with 3:2 to 100:0 v/v ethyl acetate:hexane, to give methyl 4-[2-[5-(cyclopentyloxycarbonyl)amino-2-(formyl)(methylaminophenyl]-2-oxoethyl]-3-methoxybenzoate (V) (2.12 g, 98.5%) as a foam, NMR (250 MHz, DMSO-d$_6$): 1.5–1.9[m, 8H, (CH$_2$)$_4$, 3.04(s, 2.25H, NCH$_3$, isomer A), 3.24(s, 0.75H, NCH$_3$, isomer B), 3.79, 3.82, 3.86(singlets, 6H, 2xOCH$_3$), 4.12(s, 0.5H, ArCH$_2$CO, isomer B), 4.17(s, 1.5H, ArCH$_2$CO, isomer A), 5.11(m, 1H, —OCH—), 7.27–8.15(2m, 7H), 9.85(br s, 0.25H, NH, isomer B), 9.91(br s, 0.75H, NH, isomer A).

(b) A solution of the keto-formanilide (V) (1.0 g, prepared as described in (a) above), and hydroxylamine hydrochloride (0.84 g), in freshly-distilled pyridine (100 ml) was heated and stirred under reflux for 18 hours, under a nitrogen atmosphere. The cooled solution was concentrated, the residue dissolved in ethyl acetate (100 ml), washed with water (3×25 ml), dried (MgSO$_4$) and evaporated. The product was purified by flash chromatography on silica gel (4 cm diameter column), eluting with 1:1 v/v ethyl acetate:hexane to give methyl 4-[2-[5-(cyclopentyloxycarbonyl)amino-2-methylaminophenyl]-2-(hydroxyimino)ethyl]-3-methoxybenzoate (W) (0.57 g, 59%) as an off-white solid; NMR (DMSO-d$_6$): 1.4–1.9[m, 8H, (CH$_2$)$_4$], 2.81(distorted doublet, 3H, NCH$_3$), 3.83(s, 3H, OCH$_3$), 3.92(s, 3H, OCH$_3$), 4.04(s, 2H, ArCH$_2$CO), 4.98(m, 1H, —CHO—), 6.57(d, 1H), 6.93(d, 1H), 7.24(br m, 2H), 7.46(m, 4H), 8.92 (br s, 1H, NHCO).

(c) Acetic anhydride (0.27 ml, 0.29 g) was added to a solution of the amino-oxime (W) (1.3 g, prepared as described in (b) above) and 4-(dimethylamino)pyridine (0.35 g) in dichloromethane (120 ml), under a nitrogen atmosphere. After 18 hours, the mixture was evaporated, the yellow residue dissolved in ethyl acetate (50 ml); washed with hydrochloric acid (0.05N, 15 ml), water (15 ml) and brine; dried (MgSO$_4$); and evaporated. Crystallization from ethyl acetate/hexane at −20° C. gave methyl 4-[2-(acetoxyimino)-2-[5-(cyclopentyloxycarbonyl)amino-2-methylaminophenyl]ethyl]-3-methoxybenzoate (X) (1.36 g, 96%), as a powder, mp 124°–126° C.; NMR (250 MHz, DMSO-d$_6$): 1.5–1.9[m, 8H, (CH$_2$)$_4$], 2.12(s, 3H, OCOCH$_3$), 2.83(distorted doublet, 3H, NCH$_3$), 3.83(s, 3H, OCH$_3$), 3.88(s, 3H, OCH$_3$), 4.17(s, 2H, ArCH$_2$C=N), 5.00(m, 1H, —OCH—), 6.24(d, 1H), 7.01(d, 1H), 7.3–7.5(m, 5H), 9.1(br s, 1H, NHCO).

(d) The oxime-acetate (X) (1.3 g, prepared as described in (c) above) was placed in a 100 ml round-bottomed flask charged with a stirring bar, and the flask was maintained under high vacuum by means of a vacuum pump. The flask was immersed in a preheated (170° C.) oil bath until the solid melted and for 10 minutes thereafter. The cooled product was purified by flash chromatography on silica gel (5 cm diameter column, compound applied to column by dissolution in a small volume of dichloromethane), eluting with 2:3 v/v ethyl acetate:hexane, to give methyl 4-[5-(cyclopentyloxycarbonyl)amino-1-methylindazol-3-ylmethyl]-3-methoxybenzoate (Y) (1.1 g, 96%) as a foam, NMR (250 MHz, DMSO-d$_6$): 1.5–1.9 [m, 8H, (CH$_2$)$_4$], 3.83 (s, 3H, CH$_3$), 3.92(s, 3H, CH$_3$), 3.93 (s, 3H, CH$_3$), 4.19(s, 2H, ArCH$_2$Ar), 5.07(m, 1H, —OCH—), 7.14(d, 1H), 7.35(d, 1H), 7.45–7.49(m, 3H), 7.78(br s, 1H), 9.46(br s, 1H, NH).

(e) Using a similar procedure to that described in part (d) of Example 1, except starting from the ester (Y) instead of the ester (C), 4-[5-(cyclopentyloxycarbonyl)amino-1-methylindazol-3-ylmethyl]-3-methoxybenzoic acid (U) was obtained as a white solid (95%); mp 216°–217° C.

EXAMPLE 10

Methyl 2-[4-[5-(cyclopentyloxycarbonyl)amino-1-methylindazol-3-ylmethyl]-3-methoxybenzoyl]-2-phenylsulphonylacetate Using a similar procedure to that of part (f) of Example 4 but using the acid (U) in place of the acid (J) to form a mixed anhydride and by using a similar procedure to that described in Example 4 but using the anhydride so formed in place of the anhydride (E), the title compound may be prepared.

EXAMPLE 11

5-(N'-Cyclopentylureido)-3-[2-methoxy-4-[2-(phenylsulphonyl)acetyl]benzyl]-1-methylindole Using a similar procedure to that of part (f) of Example 4 but using 4-[5-(N'-cyclopentylureido)-1-methylindol-3-ylmethyl]-3-methoxybenzoic acid (Z) in place of the acid (J) to form a mixed anhydride and by using a similar procedure to that described in Example I but using the anhydride so formed in place of the anhydride (A), the title compound may be prepared.

The starting material (Z) was obtained as follows:

(a) A solution of trichloromethyl chloroformate (0.66 g) in dry dioxan (10 ml) was added over 10 minutes to a stirred solution of methyl 4-(5-amino-1-methylindol-3-ylmethyl)-3-methoxybenzoate (S) (1.09 g) in dry dioxane (15 ml) at ambient temperature. The reaction vessel was continuously purged with nitrogen gas, and the effluent bubbled through aqueous potassium hydroxide solution to destroy excess phosgene. The in situ formation of the isocyanate of (S) was followed by TLC. After 30 minutes cyclopentylamine (0.574 g) was added, the mixture heated to 70° C. for 20 minutes, then cooled and diluted with water (100 ml). The precipitate which formed was collected by filtration, dissolved in 95:5 v/v dichloromethane:methanol (100 ml), and the solution washed with water and brine, dried (MgSO$_4$) and evaporated to give a solid which was recrystallized from acetonitrile to give methyl 4-[5-(N'-cyclopentylureido)-1-methylindol-3-ylmethyl]-3-methoxybenzoate (AA) (0.75 g, 56%) as a white solid; mp 210°–212° C.; partial NMR (250 MHz; DMSO-d$_6$): 1.25–1.80(3 m, 8H, cyclopentyl ring), 3.68(s, 3H, NCH$_3$), 3.83(s, 3H, OCH$_3$), 3.90–4.0 (2s+m, 6H, OCH$_3$, ArCH$_2$, —C$\underline{H}$NH—), 5.93(d, 1H, —CH$\underline{N}$H—).

(b) Using a similar procedure to that of part (d) of Example 1, the ester (AA) was converted into 4-[5-(N'-cyclopentylureido)-1-methylindol-3-yl-methyl]-3-methoxybenzoic acid (Z), obtained as a white powder (70%); mp 203°–206° C.

EXAMPLE 12

Methyl 2-[4-[5-(N'-cyclopentylureido)-1-methylindol-3-ylmethyl]-3-methoxybenzoyl]-2-phenylsulphonylacetate Using a similar procedure to that of part (f) of Example 4 but using the acid (Z) in place of the acid (J) to form a mixed anhydride and by using a similar procedure to that described in Example 4 but using the anhydride so formed in place of the anhydride (E), the title compound may be prepared.

EXAMPLE 13

2-[5-(N-Cyclopentylmethylcarbamoyl)-3-[2-methoxy-4-[2-(phenylsulphonyl)acetyl]benzyl]indol-1-yl]-N,N-dimethylpropionamide Using a similar procedure to that of part (f) of Example 4 but using 4-[5-(N-cyclopentylmethylcarbamoyl)-1-[1-(N,N-dimethylcarbamoyl)ethyl]indol-3-ylmethyl]-3-methoxybenzoic acid (BB) in place of the acid (J) to form a mixed anhydride and by using a similar procedure to that described in Example 1 but using the anhydride so formed in place of the anhydride (A), the title compound may be prepared.

The starting material (BB) was obtained as follows:

(a) A solution of cyclopentylnitrile (15 g) in ether (115 ml) was added dropwise, under nitrogen, to a refluxing slurry of lithium aluminum hydride (9 g) in ether (200 ml). The mixture was treated with a saturated aqueous solution of sodium sulfate and filtered. The filtrate was dried (MgSO$_4$) and evaporated to give cyclopentylmethylamine (13 g, 84%) as a yellow liquid; IR (neat): 3300, 3340, 1600 cm$^{-1}$.

(b) A solution of cyclopentylmethylamine (2.66 g), 5-carboxyindole (4.76 g), 4-(dimethylamino)pyridine (3.60 g) and 1-(3-dimethylaminopropyl)-3-ethylcarbodiimide hydrochloride (5.67 g) in methylene chloride (60 ml) was stirred for 12 hours under an atmosphere of nitrogen. The amber solution was diluted with methylene chloride (150 ml); washed successively wth 10% (w/v) aqueous sodium carbonate, 10% (v/v) hydrochloric acid, water, and brine; dried (MgSO$_4$); and evaporated. The residual amber oil was purified by flash chromatography on silica gel (700 ml), eluting with 1:3 v/v ethyl acetate:chloroform, to yield 5-(N-cyclopentylmethylcarbamoyl)indole (CC) (5.17 g, 80%) as a white crystalline solid; mp 110°–112° C.; NMR (80 MHz, CDCl$_3$): 1.0–2.4(broad m, 9H, cyclopentyl), 3.4(dd, 2H, CH$_2$N), 6.2(broad, 1H, NH), 6.6(m, 1H, H$^3$-indole), 7.3(t, 1H, H$^2$-indole), 7.4(d, 1H, H$^7$-indole), 8.5(broad, 1H, CONH).

(c) Silver(I) oxide (3.84 g) was added to a solution of the indole (CC) (3.97 g) in dioxane (30 ml). The mixture was protected from light and heated to reflux under an atmosphere of nitrogen for 2 hours. A solution of methyl 4-bromomethyl-3-methoxybenzoate (4.25 g) (prepared as described in part (a) of Example 1) in dioxane (11 ml) was added and the mixture was heated to reflux for another 4 hours. The mixture was then cooled, diluted with 1:1 v/v ethyl acetate:ether (100 ml), and filtered. The filtrate was evaporated and the residue purified by flash chromatography on silica gel (1500 ml), eluting with 1:200 v/v methanol:chloroform to give methyl 4-[5-(N-cyclopentylmethylcarbamoyl)indol-3-ylmethyl]-3-methoxybenzoate (DD) as a tan crystalline foam (2.9 g, 42%); partial NMR (80 MHz, CDCl$_3$): 3.45(dd, 2H, CH$_2$N), 3.93(s, 3H, OCH$_3$), 3.95(s, 3H, OCH$_3$), 4.17 (s, 2H, ArCH$_2$), 6.17(t, 1H, NHCO), 7.01(d, 1H, H$^2$-indole), 7.16(d, 1H), 8.04(br s, 1H, H$^4$-indole), 8.45(br s, 1H, NH).

(d) A solution of the indole (DD) (0.80 g) in N,N-dimethylformamide (2 ml) was added to a slurry of sodium hydride (0.05 g) in N,N-dimethylformamide (1 ml) at 0° C. The mixture was stirred under a nitrogen atmosphere for 20 minutes at 0° C. and for 15 minutes at 25° C. The reaction was cooled to 0° C., treated with a cold solution of N,N-dimethyl-2-bromopropanamide (0.38 g) in N,N-dimethylformamide (2 ml), and then allowed to warm to 25° C. The mixture was recooled to 0° C., quenched with saturated aqueous ammonium chloride, diluted with ethyl acetate, washed with water and brine, dried (MgSO$_4$), and evaporated. The residue was purified by flash chromatography on silica gel (600 ml), eluting with 1:99 v/v methanol:chloroform, to yield methyl 4-[5-(N-cyclopentylmethylcarbamoyl)-1-[1-(N,N-dimethylcarbamoyl)ethyl]indol-3-ylmethyl]-3-methoxybenzoate (EE) as an amber foam (0.29 g, 29%); partial NMR (80 MHz, CDCl$_3$): 1.62(d, 3H, CDCH$_3$), 2.78(s, 3H, NCH$_3$), 2.95(s, 3H, NCH$_3$), 3.39(dd, 2H, NCH$_2$), 3.89(s, 3H, OCH$_3$), 3.92 (s, 3H, OCH$_3$), 4.11(s, 2H, ArCH$_2$), 5.29(q, 1H, CH$_3$C$\underline{H}$), 7.01(s, 1H, H$^2$-indole).

(e) Using a similar procedure to that of part (d) of Example 1, the ester (EE) was converted into 4-[5-(N-cyclopentylmethylcarbamoyl)-1-[1-(N,N-dimethylcarbamoyl)ethyl]indol-3-ylmethyl]-3-methoxybenzoic acid (BB), obtained as a white solid (59%); mp 146°–147° C.

Analysis calcuated for: C$_{29}$H$_{35}$N$_3$O$_5$.0.5 H$_2$O: C, 67.68; H, 7.05; N, 8.16. Found: C, 67.67; H, 6.89; N, 7.92.

EXAMPLE 14

Methyl 2-[4-[5-(N-cyclopentylmethylcarbamoyl)-1-[1-(N,N-dimethylcarbamoyl)ethyl]indol-3-ylmethyl]-3-methoxybenzoyl]-2-phenylsulphonylacetate Using a similar procedure to that of part (f) of Example 4 but using the acid (BB) in place of the acid (J) to form a mixed anhydride and by using a similar procedure to that described in Example 4 but using the anhydride so formed in place of an anhydride (E), the title comound may be prepared.

EXAMPLE 15

The following illustrates representative pharmaceutical dosages forms which may be used for the therapeutic or prophylactic administration of an acidic compound of formula I or of a pharmaceutically acceptable salt thereof (hereinafter referred to as 'Compound X'):

| (i) | Tablet 1 | mg/tablet |
|---|---|---|
| | 'Compound X' | 100 |
| | Lactose | 182.75 |
| | Croscarmellose Sodium | 12.0 |
| | Starch | 2.25 |
| | Magnesium stearate | 3.0 |
| (ii) | Tablet 2 | mg/tablet |
| | 'Compound X' | 20 |
| | Microcrystalline cellulose | 420 |
| | Polyvinylpyrrolidone | 14.0 |
| | Starch | 43.0 |
| | Magnesium stearate | 3.0 |
| (iii) | Capsule | mg/capsule |
| | 'Compound X' | 10 |
| | Lactose | 488.5 |
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1 M Sodium hydroxide solution | 15.0% w/v |
| | Water for injection . . . to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 3.5% w/v |
| | Water for injection . . . to 100% | |
| (vi) | Aerosol | mg/ml |
| | 'Compound X' | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well known pharmaceutical techniques to accommodate differing amounts and types of active ingredient 'Compound X'. The aerosol (vi) may be used in conjunction with a standard, metered dose aerosol dispenser.

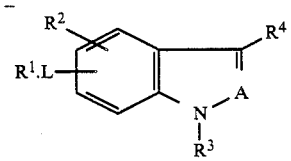

I

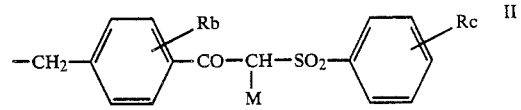

II

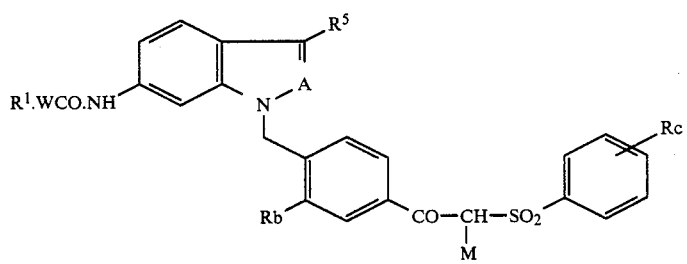

III

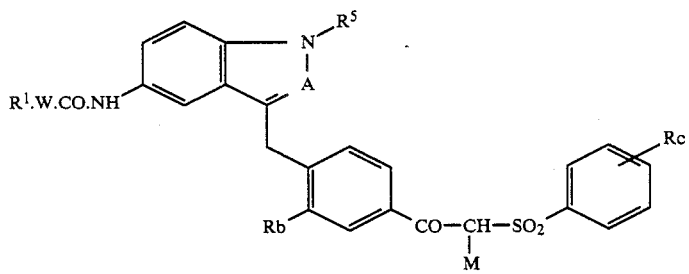

IV

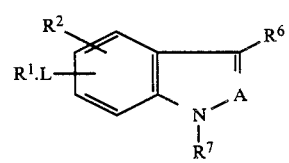

V

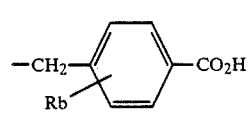

VI

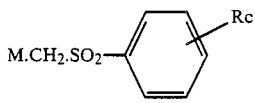 VII

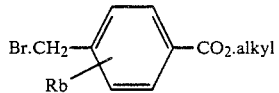 IX

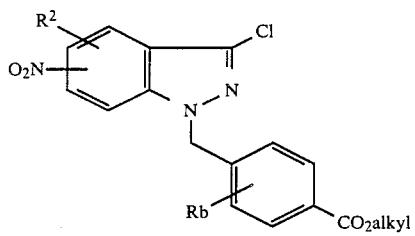 XI

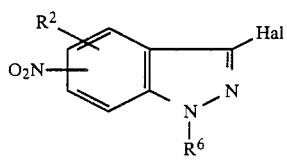 XIII

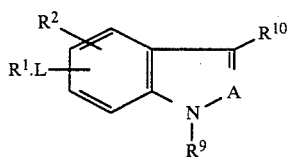 XV

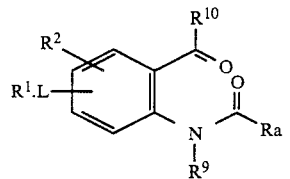 XVII

-continued

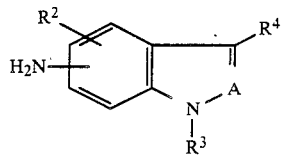 VIII

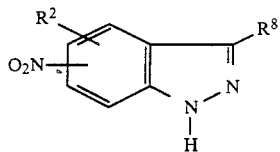 X

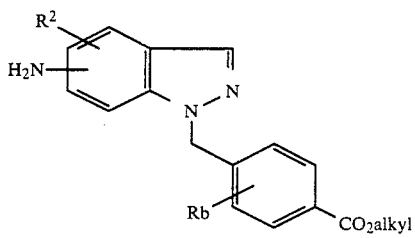 XII

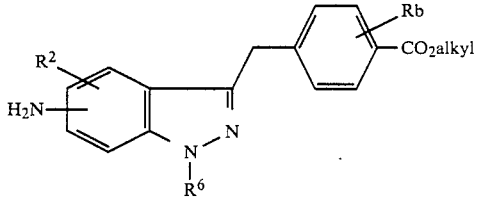 XIV

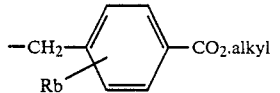 XVI

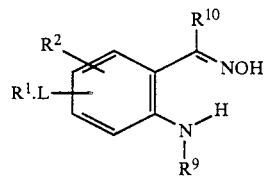 XVIII

What is claimed is:
1. A compound of formula I

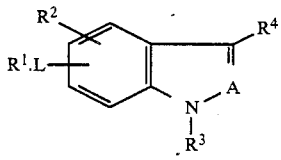 I wherein
=A— is a group of formula =C(Ra)— or =N— in which
Ra is hydrogen or (1–4C)alkyl;
the group R¹.L— is an amidic radical of formula R¹.W.CO.NH—, R¹.W.CS.NH— or R¹.NH.CO—, in which
R¹ is selected from a group consisting of (a) (2–10-C)alkyl which may contain 1 more fluorine substituents; (b) penyl-(1–6c)alkyl in which the (1–6C)alkyl moiety may bear a fluoro or (1–4C)alkoxy substituent and in which the phenyl moiety may bear a substituent selected from a group consisting of halogeno, (1–4C)alkyl, (1–4C)alkoxy and trifluoromethyl; and (c) (3–8C)cycloalkyl or (3–8C)cycloalkyl-(1–6C)alkyl, the cyclic moiety of any of which may contain one unsaturated linkage and may bear 1 or 2 (1–4C)alkyl substituents, and
W is oxy, thio, imino or a direct link to R¹;
R² is hydrogen, halogen, (1–4C)alkyl or (1–4C)alkoxy;
one of R³ and R⁴ is a radical of formula II:

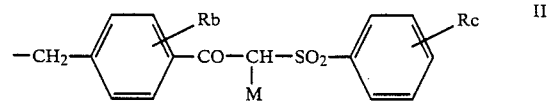 II wherein

Rb is hydrogen, (1-4C)alkyl or (1-4C)alkoxy;
Rc is hydrogen, (1-4C)alkyl, (1-4C)alkoxy, trifluoromethyl or halogeno; and
M is a hydrogen, cyano, (1-4C)alkoxycarbonyl, carbamoyl, N-phenylcarbamoyl in which the phenyl may bear a substituent selected from a group consisting of (1-4C)alkyl, halogeno and (1-4C)alkoxy, N-(1-4C)alkylcarbamoyl, N,N-di[(1-4C)alkyl]carbamoyl or (1-6C)alkanoyl;
and the other of $R^3$ and $R^4$ is hydrogen, halogeno (provided that $R^3$ may not be halogeno), (3-8C)cycloalkyl, (3-8C)cycloalkyl-(1-4C)alkyl, or (1-10C)alkyl which may contain one or two double or triple bonds, said (1-10C)alkyl additionally may bear a substituent P selected from a group consisting of cyano, carboxy, 1H-tetrazol-5-yl, (1-4C)alkoxy, (1-4C)alkoxycarbonyl, carbamoyl of formula CONRdRe, ureido of formula NRfCONRdRe, carbamoyloxy of formula (OCONRdRe, a carbamate of formula NRfCOORg, acylamino of formula NRfCORg, acyloxy of formula OCORg, and a group of formula $S(O)_n Rg$ in which for Rd, Re and Rf (1) Rd is selected from a group consisting of hydrogen, (1-6C)alkyl, and phenyl, the phenyl moiety of which may bear 1 or 2 substituents selected from a group consisting of halogeno, (1-4C)alkyl, (1-4C)alkoxy and trifluoromethyl; and Re and Rf are independently chosen from a group consisting of hydrogen and (1-6C)alkyl; or (2) Rd and Re together with the adjacent nitrogen form a pyrrole, pyrrolidine, piperidine, morpholine, piperazine or N-(1-6C)alkylpiperazine ring; and Rf is hydrogen or (1-6C)alkyl;
Rg is selected from a group consisting of (1-4C)alkyl and phenyl, the phenyl moiety of which may bear 1 or 2 substituents selected from a group consisting of halogeno, (1-4C)alkyl, (1-4C)alkoxy and trifluoromethyl; and
n is the integer 0, 1 or 2;
or a pharmaceutically acceptable salt thereof.

2. A compound as claimed in claim 1 wherein:
Ra is hydrogen or methyl;
the group $R^1.L-$ is an amidic radical of formula $R^1.W.CO.NH-$ or $R^1.NH.CO-$, in which
$R^1$ is selected from a group consisting of (a) (3-7C)alkyl which may contain 1 or more fluorine substituents; (b) phenyl-(1-4C)alkyl in which the (1-4C)alkyl moiety may bear a fluoro or (1-4C)alkoxy substituent and in which the phenyl moiety may bear a substituent selected from a group consisting of halogeno, (1-4C)alkyl, (1-4C)alkoxy and trifluoromethyl; and (c) (3-6C)cycloalkyl or (3-6C)cycloalkyl-(1-4C)alkyl, the cyclic moiety of any of which may contain one unsaturated linkage and may bear 1 or 2 (1-4C)alkyl substituents, and
W is oxy, imino or a direct link to $R^1$;
$R^2$ is hydrogen, halogeno, methyl or methoxy;
Rb is meta to the carbonyl group and is hydrogen or (1-4C)alkoxy;
Rc is hydrogen, (1-4C)alkyl or halogeno;
M is hydrogen, cyano, (1-2C)alkoxycarbonyl, carbamoyl, N-(1-2C)alkylcarbamoyl, or (1-2C)alkanoyl;
one of $R^3$ and $R^4$ is a radical of said formula II and the other of $R^3$ and $R^4$ is hydrogen, halogeno (provided that $R^3$ may not be halogeno), (3-6C)cycloalkyl, (3-6C)cycloalkyl-(1-2C)alkyl, or (1-5C)alkyl which may contain one double or triple bond, said (1-5C)alkyl which additionally may bear a substituent P selected from a group consisting of cyano, carboxy, 1H-tetrazol-5-yl, (1-2C)alkoxy, (1-2C)alkoxycarbonyl, carbamoyl of formula CONRdRe, and an oxidized thio group of formula $S(O)_n Rg$ in which for Rd and Re (1) Rd is selected from a group consisting of hydrogen, (1-4C)alkyl, and phenyl, the phenyl moiety of which may bear 1 or 2 substituents selected from a group consisting of halogeno, (1-4C)alkyl, (1-4C)alkoxy and trifluoromethyl; and Re is selected from a group consisting of hydrogen and (1-4C)alkyl; or (2) Rd and Re together with the adjacent nitrogen form a piperidine, morpholine, piperazine or N-(1-2C)alkylpiperazine ring;
Rg is selected from group consisting of (1-4C)alkyl and phenyl, the phenyl moiety of which may bear 1 or 2 substituents selected from a group consisting of halogen, (1-4C)alkyl, (1-4C)alkoxy and trifluoromethyl; and
n is the integer 1 or 2.

3. A compound as claimed in claim 2 wherein:
Rd and Re are independently chosen from a group consisting of hydrogen and (1-4C)alkyl; and
Rg is (1-4C)alkyl.

4. A compound as claimed in claim 1 wherein
$R^1$ is chosen from a group consisting of ethyl, propyl, isopropyl, butyl, isobutyl, sec-butyl, t-butyl, pentyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, alpha-fluorobenzyl, alpha-methoxybenzyl, cyclobutyl, cyclopentyl, cyclohexyl, cyclopentylmethyl, cyclohexylmethyl, 2-cyclopentylethyl, 1-cyclopentylbutyl, 1-cyclohexypropyl, 1-cyclohexylbutyl, 5-methyl-2-(1-methylethyl)cyclohexyl and 1-cyclohexen-4-methyl;
W is selected from a group consisting of oxy, imino, thio and a direct linkage;
$R^2$ is selected from a group consisting of hydrogen, fluoro, chloro, bromo, methyl and methoxy;
Ra is selected from a group consisting of hydrogen and methyl;
Rb is selected from a group consisting of hydrogen, methyl and methoxy;
Rc is selected from a group consisting of hydrogen, methyl, methoxy, chloro and bromo;
Rd, Re and Rf are selected from one of the following:
(1) Rd is selected from a group consisting of hydrogen, methyl, ethyl, propyl, isopropyl, t-butyl, phenyl, 2-methylphenyl and 4-chlorophenyl; and Re and Rf are each independently selected from a group consisting of hydrogen, methyl and ethyl; and (2) Rd and Re together with the adjacent nitrogen form a ring selected from a group consisting of piperidine, morpholine, and N-methylpiperazine; and Rf is selected from a group consisting of hydrogen, methyl and ethyl; Rg is selected from a group consisting of methyl, ethyl, propyl, isopropyl, phenyl, 2-methylphenyl and 4-chlorophenyl; and
M is selected from a group consisting of hydrogen, cyano, methoxycarbonyl, ethoxycarbonyl, carbamoyl, N-phenylcarbamoyl, N-methylcarbamoyl, N,N-dimethylcarbamoyl and acetyl.

5. A compound as claimed in claim 1 wherein $R^1$ is selected from a group consisting of (a) ethyl, propyl, isopropyl, butyl, isobutyl, sec-butyl, t-butyl, pentyl, 1-ethylpropyl, hexyl, heptyl, 1-ethylpentyl and nonyl, wherein each group may be substituted by at least one flourine; (b) benzyl, 1-phenylethyl, 2-phenylethyl, 1-phenylpropyl, 2-phenylpropyl, 3-phenylpropyl, 1-methyl-1-phenylethyl, 1-phenylbutyl and 1-phenylpentyl, wherein the alkyl portion may be substituted by methoxy or ethoxy and the phenyl moiety may be substituted by a number selected from a group consisting of fluoro, chloro, bromo, methyl, ethyl, methoxy and ethoxy; (c) cyclopropyl, cyclobutyl, cyclopentyl, cyclohexyl, cycloheptyl, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl, and 1-cyclohexylbutyl; and (d) cyclopentenyl, cyclohexenyl, cyclopentenylmethyl, 1-cyclohexen-4-ylmethyl and 1-(cyclohexenyl)butyl; which may be substituted on the cyclic moiety by methyl, ethyl or isopropyl;

M is selected from a group consisting of methoxycarbonyl, ethoxycarbonyl, N-methylcarbamoyl, N-ethylcarbamoyl, N,N-dimethylcarbamoyl, N-phenylcarbamoyl, N-p-tolycarbamoyl, N-p-chlorophenylcarbamoyl, N-o-tolylcarbamoyl, N-p-anisylcarbamoyl, acetyl, propionyl, and butyryl.

6. A compound as claimed in claim 1 wherein
$R^1$ is selected from a group consisting of 1-ethylpentyl, cyclopentyl and cyclopentylmethyl;
$R^2$ is hydrogen;
one of $R^3$ and $R^4$ is a radical of said formula II and the other of $R^3$ and $R^4$ is selected from a group consisting of hydrogen, methyl, ethyl, and 1-(N,N-dimethylcarbamoyl)ethyl;
Rb is methoxy;
Rc is hydrogen; and
M is selected from a group consisting of hydrogen, cyano and methoxycarbonyl.

7. A compound as claimed in claim 1 wherein
$R^1$ is selected from a group consisting of 1-ethylpentyl, cyclopentyl, and cyclopentylmethyl;

$R^2$ is hydrogen;
one of $R^3$ and $R^4$ is a radical of said formula II and the other of $R^3$ and $R^4$ is selected from a group consisting of hydrogen, methyl, and ethyl;
Rb is methoxy;
Rc is hydrogen; and
M is selected from a group consisting of hydrogen, cyano, and methoxycarbonyl.

8. A compound as claimed in claim 1 wherein
$R^1$ is selected from a group consisting of butyl, pentyl, 1-ethylpentyl, 1-phenylpropyl, alphafluorobenzyl, alpha-methoxybenzyl, cyclopentyl and cyclopentylmethyl;
W is selected from a group consisting of oxy, imino and a direct linkage;
$R_2$, Ra and Rc are each hydrogen;
Rb is methoxy; and
M is selected from a group consisting of hydrogen and methoxycarbonyl.

9. A compound as claimed in claim 1 selected from a group consisting of
(a) compounds of formula I wherein $R^1.L$ is $R^1.W.CO.NH—$, W is oxy or imino and $R^1$ is cyclopentyl;
(b) compounds of formula I wherein $R^1.L$ is $R^1.W.CO.NH—$, W is a direct link and $R^1$ is 1-ethylpentyl or cyclopentylmethyl;
(c) compounds of formula I wherein $R^1.L$ is $R^1.NH.CO—$ and $R^1$ is cyclopentylmethyl;
(d) compounds of formula I wherein $R^1.L$ is $R^1.NH.CO—$ and one of $R^3$ and $R^4$ is a radical of said formula II and the other of $R^3$ and $R^4$ is (1-10-C)alkyl which may contain one or two triple bonds and bearing said substituent P.

10. A compound of formula III

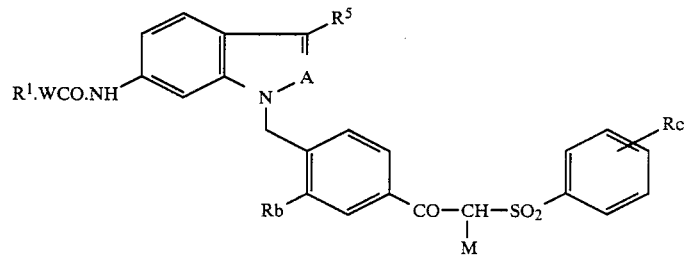

wherein $R^1$, W, A, Rb, Rc and M have the meanings defined in claim 1 and $R^5$ has a value as defined for $R^3$ or $R^4$ in claim 1, provided that $R^5$ may not be a radical of said formula II, or a pharmaceutically acceptable salt thereof.

11. A compound of formula IV

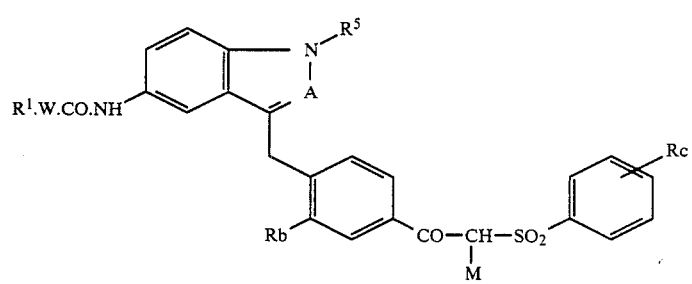

wherein $R^1$, W, A, Rb, Rc, and M have the meanings defined in claim 1 and $R^5$ has a value as defined for $R^3$ or $R^4$ in claim 1, provided that $R^5$ may not be a radical of said formula II, or a pharmaceutically acceptable salt thereof.

12. A compound as claimed in claim 1 which is methyl 2-[4-[6-(cyclopentyloxycarbonyl)aminoindazol-1-ylmethyl]-3-methoxy-benzoyl]-2-phenylsulphonylacetate or a pharmaceutically acceptable salt thereof.

13. A salt as claimed in any one of the preceding claims 1-9 which is a salt with a base forming a physiologically acceptable cation.

14. A pharmaceutical composition comprising a leukotriene antagonizing amount of a compound of claim 1 or a pharmaceutically acceptable salt thereof and a non-toxic pharmaceutically acceptable diluent or carrier.

15. A composition as claimed in claim 14 wherein said composition is in the form of a liquid or powdered aerosol.

16. A method of antagonizing at least one of the actions of at least one type of leukotriene in a mammal comprising administering to the mammal a leukotriene antagonizing amount of a compound of claim 1.

17. A method for the treatment of a selected allergic or inflammatory disorder in a mammal comprising administering a leukotriene antagonizing amount of a compound of claim 1 to a mammal in need of such treatment.

* * * * *